(12) United States Patent
Utashima et al.

(10) Patent No.: US 10,913,971 B2
(45) Date of Patent: *Feb. 9, 2021

(54) ENZYME PREPARATION FOR USE IN MEASUREMENT OF GLUCOSE

(71) Applicant: TOYOBO CO., LTD., Osaka (JP)

(72) Inventors: Yuu Utashima, Tsuruga (JP); Takahide Kishimoto, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/555,394

(22) PCT Filed: Apr. 7, 2016

(86) PCT No.: PCT/JP2016/061370
§ 371 (c)(1),
(2) Date: Sep. 1, 2017

(87) PCT Pub. No.: WO2016/163448
PCT Pub. Date: Oct. 13, 2016

(65) Prior Publication Data
US 2018/0066302 A1    Mar. 8, 2018

(30) Foreign Application Priority Data
Apr. 9, 2015 (JP) ................. 2015-079812

(51) Int. Cl.
| | | |
|---|---|---|
| C12Q 1/54 | (2006.01) | |
| C12Q 1/32 | (2006.01) | |
| C12N 9/04 | (2006.01) | |
| C12N 9/24 | (2006.01) | |
| C12M 1/34 | (2006.01) | |
| G01N 27/327 | (2006.01) | |

(52) U.S. Cl.
CPC ............. *C12Q 1/54* (2013.01); *C12M 1/34* (2013.01); *C12N 9/0006* (2013.01); *C12N 9/2402* (2013.01); *C12Q 1/32* (2013.01); *C12Y 101/05* (2013.01); *G01N 27/327* (2013.01); *G01N 2333/904* (2013.01)

(58) Field of Classification Search
CPC ...... C12Y 101/05; C12Y 302/01; C12Q 1/32; C12Q 1/54; C12N 9/0006; C12N 9/2402; G01N 27/327
See application file for complete search history.

(56) References Cited

U.S. PATENT DOCUMENTS

| | | | |
|---|---|---|---|
| 7,067,295 B1 | 6/2006 | Sode | |
| 7,494,494 B2 | 2/2009 | Stoianovici et al. | |
| 7,514,250 B2 | 4/2009 | Omura et al. | |
| 7,553,649 B2 | 6/2009 | Tsuji et al. | |
| 7,662,600 B2 | 2/2010 | Kawaminami et al. | |
| 7,871,805 B2 * | 1/2011 | Aiba .................... | C12N 9/0006 435/193 |
| 8,039,248 B2 | 10/2011 | Kawaminami et al. | |
| 8,445,246 B2 | 5/2013 | Tajima et al. | |
| 8,691,547 B2 | 4/2014 | Omura et al. | |
| 8,945,359 B2 | 2/2015 | Honda et al. | |
| 9,260,699 B2 | 2/2016 | Sumida et al. | |
| 9,404,144 B2 | 8/2016 | Sumida et al. | |
| 9,487,758 B2 | 11/2016 | Sumida et al. | |
| 9,506,042 B2 | 11/2016 | Sumida et al. | |
| 9,657,325 B2 | 5/2017 | Aiba et al. | |
| 9,796,963 B2 | 10/2017 | Yamazaki et al. | |
| 2006/0063217 A1 | 3/2006 | Omura et al. | |
| 2007/0105174 A1 | 5/2007 | Aiba et al. | |
| 2008/0003628 A1 | 1/2008 | Kitabayashi et al. | |
| 2008/0014611 A1 | 1/2008 | Kitabayashi et al. | |
| 2008/0014612 A1 | 1/2008 | Tsuji et al. | |
| 2008/0020426 A1 | 1/2008 | Aiba et al. | |
| 2008/0090278 A1 | 4/2008 | Kitabayashi et al. | |
| 2008/0220460 A1 | 9/2008 | Kawaminami et al. | |
| 2009/0176262 A1 | 7/2009 | Omura et al. | |
| 2009/0259024 A1 | 10/2009 | Tsuji et al. | |
| 2009/0317848 A1 | 12/2009 | Kawaminami et al. | |
| 2010/0297743 A1 | 11/2010 | Omura et al. | |
| 2011/0020851 A1 | 1/2011 | Aiba et al. | |
| 2011/0033880 A1 | 2/2011 | Yada et al. | |
| 2011/0045513 A1 * | 2/2011 | Takenaka ............... | C07K 14/80 435/14 |

(Continued)

FOREIGN PATENT DOCUMENTS

| | | |
|---|---|---|
| EP | 1862543 A1 | 12/2007 |
| JP | 2001-233817 A | 8/2001 |

(Continued)

OTHER PUBLICATIONS

Bak et al., "Studies on the glucose dehydrogenase of *Aspergillus oryzae*. I. Induction of its synthesis by p-benzoquinone and hydroquinone," *Biochim. Biophys. Acta.*, 139: 265-276 (1967).
Bak, "Studies on glucose dehydrogenase of *Aspergillus oryzae*. II. Purification and physical and chemical properties," *Biochim. Biophys. Acta.*, 139(2): 277-293 (1967).
Friedman, "The Purification and Properties of Trehalase Isolated from *Phormia regina*, Meig.," *Arch. Biochem. Biophys.*, 87: 252-258 (1960).
Utashima et al., "Heterologous expression of FAD-dependent glucose dehydrogenase from *Aspergillus oryzae* in a basidiomycete yeast *Cryptococcus* cp. S-2," *Abstract of the Annual Meeting of the Society for Biotechnology, Japan*, 65: 28, abstract 1P-044 (2013).
White et al., "A Glucose Oxidase Reagent for Maltase Assay," *Anal. Biochem.*, 2: 380-384 (1961).

(Continued)

Primary Examiner — Thane Underdahl
(74) *Attorney, Agent, or Firm* — Leydig, Voit & Mayer, Ltd.

(57) ABSTRACT

Provided is GDH with increased applicability to glucose sensors. A composition contains FADGDH, wherein when 0.1 mL of the composition is added to 2.9 mL of a solution containing 10 mM of trehalose and 1 mmol/L of potassium ferricyanide to give a glucose dehydrogenase activity of 500 U/mL and incubated at 37° C., the decrease in absorbance at 405 nm resulting from reduction of the potassium ferricyanide is less than 20 mAbs per minute.

21 Claims, 1 Drawing Sheet
Specification includes a Sequence Listing.

(56) References Cited

U.S. PATENT DOCUMENTS

| | | |
|---|---|---|
| 2011/0053194 A1 | 3/2011 | Yuuki et al. |
| 2011/0136158 A1 | 6/2011 | Takenaka et al. |
| 2011/0318810 A1 | 12/2011 | Tajima et al. |
| 2012/0122130 A1 | 5/2012 | Omura et al. |
| 2012/0171708 A1 | 7/2012 | Kawaminami et al. |
| 2012/0244565 A1 | 9/2012 | Nishio et al. |
| 2013/0168263 A1 | 7/2013 | Sode et al. |
| 2013/0183716 A1 | 7/2013 | Kawano et al. |
| 2013/0309750 A1 | 11/2013 | Tajima et al. |
| 2014/0057331 A1 | 2/2014 | Tajima et al. |
| 2014/0154777 A1 | 6/2014 | Sumida et al. |
| 2014/0234533 A1 | 8/2014 | Omura et al. |
| 2014/0287445 A1 | 9/2014 | Tajima et al. |
| 2014/0287478 A1 | 9/2014 | Sumida et al. |
| 2015/0024461 A1 | 1/2015 | Nishio et al. |
| 2015/0031059 A1 | 1/2015 | Sumida et al. |
| 2015/0111280 A1 | 4/2015 | Sumida et al. |
| 2015/0152394 A1 | 6/2015 | Honda et al. |
| 2015/0240216 A1 | 8/2015 | Yamazaki et al. |
| 2015/0267178 A1 | 9/2015 | Ozawa et al. |
| 2016/0265021 A1 | 9/2016 | Aiba et al. |
| 2018/0030498 A1 | 2/2018 | Utashima |

FOREIGN PATENT DOCUMENTS

| | | |
|---|---|---|
| JP | 2003-261591 A | 9/2003 |
| JP | 2007-289148 A | 11/2007 |
| JP | 2008-237210 A | 10/2008 |
| JP | 4292486 B2 | 7/2009 |
| JP | 4348563 B2 | 10/2009 |
| JP | 2010-054503 A | 3/2010 |
| JP | 2010-057427 A | 3/2010 |
| JP | 4494978 B2 | 6/2010 |
| JP | 4648993 B2 | 3/2011 |
| JP | 2011-139677 A | 7/2011 |
| JP | 2013-081399 A | 5/2013 |
| JP | 2013-090621 A | 5/2013 |
| JP | 2013-116102 A | 6/2013 |
| JP | 2013-135663 A | 7/2013 |
| JP | 2013-150590 A | 8/2013 |
| JP | 5408125 B2 | 2/2014 |
| WO | WO 2000/055349 A1 | 9/2000 |
| WO | WO 2004/058958 A1 | 7/2004 |
| WO | WO 2006/101239 A1 | 9/2006 |
| WO | WO 2007/116710 A1 | 10/2007 |
| WO | WO 2008/001903 A1 | 1/2008 |
| WO | WO 2008/059777 A1 | 5/2008 |
| WO | WO 2009/069381 A1 | 6/2009 |
| WO | WO 2010/053161 A1 | 5/2010 |
| WO | WO 2010/126139 A1 | 11/2010 |
| WO | WO 2010/140431 A1 | 12/2010 |
| WO | WO 2011/004654 A1 | 1/2011 |
| WO | WO 2011/034108 A1 | 3/2011 |
| WO | WO 2011/068050 A1 | 6/2011 |
| WO | WO 2012/001976 A1 | 1/2012 |
| WO | WO 2012/073986 A1 | 6/2012 |
| WO | WO 2012/073987 A1 | 6/2012 |
| WO | WO 2012/169512 A1 | 12/2012 |
| WO | WO 2013/022074 A1 | 2/2013 |
| WO | WO 2013/031664 A1 | 3/2013 |
| WO | WO 2013/051682 A1 | 4/2013 |
| WO | WO 2013/065623 A1 | 5/2013 |
| WO | WO 2013/118798 A1 | 8/2013 |
| WO | WO 2013/147206 A1 | 10/2013 |
| WO | WO 2014/045912 A1 | 3/2014 |
| WO | WO 2016/035849 A1 | 3/2016 |

OTHER PUBLICATIONS

Japanese Patent Office, International Search Report in International Application No. PCT/JP2016/061370 (May 17, 2016).
Bak, "Studies on glucose dehydrogenase of Aspergillus oryzae III. General enzymatic properties," *Biochim. Biophys. Acta*, 146(2): 317-327 (1967).
Bak et al., "Studies on glucose dehydrogenase of Aspergillus oryzae IV. Histidyl residue as an active site," *Biochim. Biophys. Acta*, 146(2): 328-335 (1967).
Chica et al., "Semi-rational approaches to engineering enzyme activity: combining the benefits of directed evolution and rational design," *Curr. Opin. Biotechnol.*, 16(4): 378-384 (2005).
Devos et al., "Practical Limits of Function Prediction," *Proteins*, 41(1): 98-107 (2000).
Gan et al., "Choline Dehydrogenase [Colletotrichum gloeosporioides Nara gc5]", National Center for Biotechnology Information, Protein Database [online], GenBank Database Accession No. ELA34144 (Dec. 14, 2012).
Griebenow et al., "Lyophilization-induced reversible changes in the secondary structure of proteins," *Proc. Natl. Acad. Sci. U.S.A.*, 92(24): 10969-10976 (1995).
Guo et al., "Protein tolerance to random amino acid change," *Proc. Natl. Acad. Sci. U.S.A.*, 101(25): 9205-9210 (2004).
Hayano et al., "Purification and Properties of 3-Ketosucrose-forming Enzyme from the Cells of *Agrobacterium tumefaciens*," *The Journal of Biological Chemistry*, 242(16): 3665-3672 (1967).
Kisselev, "Polypeptide Release Factors in Prokaryotes and Eukaryotes: Same Function, Different Structure," *Structure*, 10(1): 8-9 (2002).
Machida et al., "Genome sequencing and analysis of Aspergillus oryzae," *Nature*, 438(7071): 1157-1161 (2005).
Sen et al., "Developments in Directed Evolution for Improving Enzyme Functions," *Appl. Biochem. Biotechnol.*, 143(3): 212-223 (2007).
Seffernick et al., "Melamine Deaminase and Atrazine Chlorohydrolase: 98 Percent Identical but Functionally Different," *J. Bacteriol.*, 183(8): 2405-2410 (2001).
Sygmund et al., "Heterologous overexpression of *Glomerella cingulata* FAD-dependent glucose dehydrogenase in *Escherichia coli* and *Pichia pastoris*," *Microb. Cell Fact.*, 10: 106 (2011).
Sygmund et al., "Reduction of quinones and phenoxy radicals by extracellular glucose dehydrogenase from *Glomerella cingulata* suggests a role in plant pathogenicity," *Microbiology*, 157(Pt 11): 3203-3212 (2011).
Tang et al., "Design of Freeze-Drying Processes for Pharmaceuticals: Practical Advice", *Pharmaceutical Research*, 21(2): 191-200 (2004).
Tsugawa et al., "Purification of a marine bacterial glucose dehydrogenase from *Cytophaga marinoflava* and its application for measurement of 1,5-anhydro-D-glucitol," *Applied Biochemistry and Biotechnology*, 56(3):301-310 (1996).
Tsugawa et al., "Fluorescent measurement of 1,5-anhydro-D-glucitol based on a novel marine bacterial glucose dehydrogenase," *Enzyme and Microbial Technology*, 22(4): 269-274 (1998).
Whisstock et al., "Prediction of protein function from protein sequence and structure," *Q. Rev. Biophys.*, 36(3): 307-340 (2003) [abstract only].
Witkowski et al., "Conversion of a β-Ketoacyl Synthase to a Malonyl Decarboxylase by Replacement of the Active-Site Cysteine with Glutamine," *Biochemistry*, 38(36): 11643-11650 (1999).
Zafar et al., "Electron-Transfer Studies with a New Flavin Adenine Dinucleotide Dependent Glucose Dehydrogenase and Osmium Polymers of Different Redox Potentials" *Anal. Chem.*, 84(1):334-341 (2012).
Japanese Patent Office, International Search Report in International Patent Application No. PCT/JP2012/070385 (dated Sep. 4, 2012).
Japanese Patent Office, International Search Report in International Patent Application No. PCT/JP2012/077848 (dated Jan. 15, 2013).
Japanese Patent Office, International Search Report in International Patent Application No. PCT/JP2013/052798 (dated Mar. 5, 2013).
Japanese Patent Office, International Search Report in International Patent Application No. PCT/JP2013/067309 (dated Jul. 23, 2013).
Japanese Patent Office, International Search Report in International Patent Application No. PCT/JP2013/074067 (dated Nov. 12, 2013).
Japanese Patent Office, International Search Report in International Patent Application No. PCT/JP2014/077223 (dated Jan. 6, 2015).
Japanese Patent Office, International Search Report in International Search Report in International Patent Application No. PCT/JP2016/050913 (dated Apr. 12, 2016).

(56) References Cited

OTHER PUBLICATIONS

Toyobo Co., Ltd., "Ideas & Chemistry: *E. coil* Competent Cell Kit—Competent high DH5α (Code No. DNA-903)" [downloaded from http://lifescience.toyobo.co.jp/user_data/pdf/products/manual/DNA-903.pdf on Jun. 26, 2019].
U.S. Appl. No. 15/650,528, filed Jul. 14, 2017.
U.S. Appl. No. 11/692,678, filed Mar. 28, 2007.
U.S. Appl. No. 14/176,701, filed Feb. 10, 2014.
U.S. Appl. No. 14/266,304, filed Apr. 30, 2014.
U.S. Appl. No. 14/374,164, filed Jul. 23, 2014.
U.S. Appl. No. 14/426,679, filed Sep. 6, 2013.
U.S. Appl. No. 14/584,552, fled Dec. 29, 2014.
U.S. Appl. No. 15/134,684, filed Apr. 21, 2016.
Satake et al., "Novel glucose dehydrogenase from *Mucor prainii*: Purification, characterization, molecular cloning and gene expression in *Aspergillus sojae*," *J. Biosci. Bioeng.*, 120(5): 498-503 (2015).
Yu, "Research on the production of clinical testing enzymes by using microorganisms," Doctoral Dissertation, Hiroshima University (Mar. 2015).
Japanese Patent Office, Notice of Reasons for Refusal in Japanese Patent Application No. 2017-511045 (dated Jun. 2, 2020).

\* cited by examiner

ENZYME PREPARATION FOR USE IN MEASUREMENT OF GLUCOSE

CROSS-REFERENCE TO RELATED APPLICATIONS

This patent application is the U.S. national phase of International Patent Application No. PCT/JP2016/061370, filed on Apr. 7, 2016, which claims the benefit of Japanese Patent Application No. 2015-079812, filed Apr. 9, 2015, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 26,695 bytes ASCII (Text) file named "730704Sequence-Listing.txt," created Aug. 29, 2017.

TECHNICAL FIELD

The present invention relates to preparations containing an enzyme for measuring glucose, and the use of the preparations.

BACKGROUND ART

Measurement of blood glucose concentration is essential for diabetic patients to suitably control their blood sugar levels. Daily-use devices for checking blood glucose concentrations include simple blood-glucose-concentration self-monitors (glucose sensors) and measurement kits. For example, devices using enzymes, such as glucose oxidase (hereinafter, may also be referred to as GOD) or glucose dehydrogenase (hereinafter, may also be referred to as GDH), are known. Due to the difference of coenzymes required for reaction, a variety of GDHs, such as nicotinamide-dependent GDH, pyrroloquinoline quinine (hereinafter, may also be referred to as PQQ)-dependent GDH, and flavin adenine dinucleotide (hereinafter, may also be referred to as FAD)-dependent GDH, are known. To improve their substrate specificity or stability, these GDHs have been genetically modified with a suitable host vector system, or the amino acid sequences of these GDHs have also been partly modified (e.g., PTL 1 to 6 for an FAD-dependent GDH, which hereinafter may also be referred to as FADGDH).

CITATION LIST

Patent Literature

PTL 1: U.S. Pat. No. 4,494,978
PTL 2: U.S. Pat. No. 4,292,486
PTL 3: U.S. Pat. No. 4,648,993
PTL 4: JP2013-90621A
PTL 5: JP2013-116102A
PTL 6: U.S. Pat. No. 5,408,125

SUMMARY OF INVENTION

Technical Problem

As stated above, studies have been conducted on a variety of glucose-measuring enzymes for measuring blood glucose concentrations, and glucose-measuring-enzyme preparations containing these enzymes have been developed and become commercially available. Glucose sensors using these enzyme preparations have also been produced. These sensors, however, may involve problems that are not expected from the physicochemical characteristics of glucose-measuring enzymes contained in the preparations for use. An analysis by the present inventors revealed, for example, the following issues: different manufactured glucose sensors may result in different calculations, and some may give a higher measured value than the actual glucose concentration of the sample; or blank-up may occur. An object of the present invention is to provide glucose-measuring-enzyme preparations that have increased applicability to glucose sensors by solving these problems, and to enable accurate and simple glucose measurement.

Solution to Problem

From glucose-measuring enzymes, the present inventors selected, as a research target, FADGDH, which is not affected by dissolved oxygen and less vulnerable to maltose, etc., and examined factors that affect the fluctuations of blank values lying in glucose sensors (factors other than those lying in the glucose-measuring enzymes), using glucose-measuring-enzyme preparations used in glucose sensors showing high blank values. The results indicated that one of the factors is the formulation of glucose sensors; in particular, glucose sensors to which trehalose has been added in production are likely to show high blank values.

The inventors also examined factors that affect fluctuations of blank values lying in glucose-measuring enzymes, using glucose sensors to which trehalose had been added. The results indicated that trehalase contamination in glucose-measuring-enzyme preparations is likely to lead to high blank values.

From the results, the inventors speculated as follows.

Because enzyme preparations containing FADGDH (hereinafter, may also be referred to as "FADGDH preparation") are obtained through purification from their original organisms or host organisms, the preparations may contain a slight amount of proteins intrinsic to those organisms. When that is the case, insufficient purification of FADGDH may bring the proteins into FADGDH preparations. Such contaminating proteins may possibly include proteins that cause defects in glucose sensors when incorporated into the sensors. For example, when glucose is measured with a glucose sensor using a FADGDH preparation that contains an amount of an enzyme that hydrolyzes sugar (trehalase in the case described above), an oligosaccharide (trehalose in the case described above) that can serve as a substrate for the glycoside hydrolase present in the sample to thereby generate glucose is degraded to produce glucose, which is then subjected to oxidation by FADGDH. This may possibly result in calculation of a higher measured value than the actual glucose concentration of the sample.

FADGDH preparations for use in glucose sensors may contain additives for various purposes. In that case, when a glycoside hydrolase is present in an FADGDH preparation, and the glucose sensor contains an oligosaccharide that can serve as a substrate for the glycoside hydrolase to produce glucose, even a trace amount of the glycoside hydrolase degrades the oligosaccharide and produces glucose over a prolonged storage period. The glucose is then subjected to oxidation by FADGDH, possibly leading to the blank-up of glucose measurement kits or glucose sensors.

The present inventors further conducted extensive research based on this speculation and found that producing a FADGDH preparation from which various oligosaccharide hydrolases have been removed through purification to enhance the purity, in particular a FADGDH-containing composition with suppressed trehalose degradation activity, can avoid the risk of false high values or blank-up. The inventors then completed the invention.

Specifically, the present invention is set forth as follows.

Item 1.

A composition comprising flavin adenine dinucleotide-dependent glucose dehydrogenase (FADGDH), wherein when 0.1 mL of the composition is added to 2.9 mL of a solution containing 10 mM of trehalose and 1 mmol/L of potassium ferricyanide to give a glucose dehydrogenase activity of 500 U/mL and incubated at 37° C., a decrease in absorbance at 405 nm resulting from reduction of the potassium ferricyanide is less than 20 mAbs per minute.

Item 2.

A composition comprising flavin adenine dinucleotide-dependent glucose dehydrogenase (FADGDH), the composition having a trehalase content of 2.0% or less.

Item 3.

A glucose measurement sensor comprising the composition according to Item 1 or 2.

Item 4.

A method for measuring glucose using the composition according to Item 1 or 2.

Item 5.

A method for measuring glucose using the glucose measurement sensor according to Item 3.

Advantageous Effects of Invention

The present invention made it possible to provide a glucose dehydrogenase composition (preparation) that is not affected by trehalose contamination in a sample or trehalose contained as an additive. Because a preparation with this characteristic enables more accurate measurement, the preparation is preferable as a glucose-measuring-enzyme preparation, and particularly preferable as an enzyme preparation for glucose sensors. Thus, the use of the glucose-measuring-enzyme preparation of the present invention made it possible to provide highly accurate kits for quantifying glucose and highly accurate glucose sensors.

DESCRIPTION OF EMBODIMENTS

An embodiment of the present invention is a composition comprising flavin adenine dinucleotide-dependent glucose dehydrogenase (FADGDH), wherein when 0.1 of the composition is added to 2.9 mL of a solution containing 10 mM of trehalose and 1 mmol/L of potassium ferricyanide to give a glucose dehydrogenase activity of 500 U/mL and incubated at 37° C., a decrease in absorbance at 405 nm resulting from reduction of the potassium ferricyanide is less than 20 mAbs per minute.

The decrease in absorbance at 405 nm is expressed as a decrease in absorbance at 405 nm caused by reduction of potassium ferricyanide to potassium ferrocyanide occurring in parallel with the oxidation of glucose, which is generated by the hydrolysis of trehalose, by a glucose dehydrogenase to form gluconolactone. Specifically, the decrease in absorbance is measured by the "trehalose hydrolysis activity measurement method" described later. Hereinafter, measuring the decrease in absorbance at 405 nm by this method is also called a "test of the present invention." A lower decrease in absorbance in the test of the present invention indicates a lower trehalose degradation activity in the composition.

The degree of the decrease in absorbance in the test of the present invention reflects the content of a trehalose degrading enzyme (typically trehalase) in the composition. This means that as the decrease in absorbance in the test of the present invention is lower, the composition contains a lower amount of a trehalose degrading enzyme relative to FADGDH.

Specifically, another embodiment of the present invention is a composition comprising flavin adenine dinucleotide-dependent glucose dehydrogenase (FADGDH) wherein the content of a trehalase is 2.0% or less.

One of the attributes that must be present in the composition of the present invention is that the decrease in absorbance at 405 nm in the test of the present invention is less than 20 mAbs per minute. The decrease in absorbance is more preferably less than 10 mAbs per minute, still more preferably less than 5 mAbs per minute, yet more preferably less than 4 mAbs per minute, and still more preferably less than 2 mAbs per minute; and most preferably, the decrease in absorbance is not substantially detected.

That is, one of the characteristics of the composition of the present invention described above is also described as follows: the amount of a trehalose degrading enzyme is extremely low. Specifically, the composition of the present invention may have a property such that "the content of a trehalase is 2.0% or less," instead of the property regarding the decrease in absorbance. The content of the trehalase is more preferably 1.0% or less, still more preferably 0.8% or less, and still more preferably 0.76% or less; and most preferably, trehalase is substantially not detected.

Another attribute must be present in the composition of the present invention is that the composition contains FADGDH.

A variety of known FADGDH can be used as FADGDH for the present invention, and FADGDH is not particularly limited. Examples of FADGDH include FADGDH derived from filamentous fungi. Preferable examples of FADGDH derived from filamentous fungi include *Aspergillus*-derived FADGDH, *Penicillium*-derived FADGDH, *Trichoderma*-derived FADGDH, *Colletotrichum*-derived FADGDH, and *Mucor*-derived FADGDH. More preferable examples include *Aspergillus*-derived FADGDH, *Penicillium*-derived FADGDH, and *Mucor*-derived FADGDH. Still more preferable examples include *Aspergillus*-derived GDH. Of *Aspergillus*-derived GDHs, *Aspergillus-oryzae* derived GDH (e.g., GDH indicated by SEQ ID: No. 1), and *Aspergillus terreus*-derived GDH (e.g., GDH indicated by SEQ ID: No. 2) are particularly preferable. Alternatively, *Mucor*-derived GDH is still more preferable. Of *Mucor*-derived GDHs, *Mucor subtilissimus*-derived GDH (e.g., GDH indicated by SEQ ID: No. 3), *Mucor hiemalis*-derived GDH (GDH indicated by SEQ ID: No. 4), and *Mucor* RD056860-derived GDH (e.g., GDH indicated by SEQ ID: No. 5) are particularly preferable.

The FADGDH listed above can be expressed in a range of hosts, and the host is not particularly limited. Known hosts include genus *Aspergillus*, genus *Cryptococcus*, and yeasts, and a host can suitably be selected from these hosts. The expression vector applied to the hosts is also not particularly limited, and a known expression vector can suitably be selected for use. A host of *Aspergillus* can be produced with reference to, for example, the method described in Example 4 of WO2006/101239. A host of *Cryptococcus* can be produced with reference to, for example, the method described in the Examples of WO2013/135663. A host of a yeast (e.g., genus *Zygosaccharomyces*) can be produced with reference to, for example, the method described in Example 7 of WO2012/073986.

In this specification, the activity of FADGDH is defined by the "FADGDH activity measurement method" described later.

The method for producing "a FADGDH-containing composition, wherein the decrease in absorbance at 405 nm is less than 20 mAbs per minute in the test of the present invention," or "a FADGDH-containing composition, wherein the content of a trehalase is 2.0% or less" described above is not particularly limited. Examples include a method in which a fraction showing trehalose hydrolysis activity is isolated from a FADGDH-containing composition by various types of chromatography. Examples of usable chromatography include ion-exchange chromatography, gel filtration chromatography, and hydrophobic chromatography. Of these, preferable is ion-exchange chromatography, examples of which include cation-exchange chromatography and anion-exchange chromatography. The former can be performed using an ion exchanger, for example, an ion exchanger packed with a carrier to which carboxy methyl groups are bound (e.g., a CM-Sepharose column). The latter can be performed using an ion exchanger, for example, an ion exchanger packed with a carrier to which sulfopropyl groups are bound (e.g., an SP-Sepharose column). Of these, hydrophobic chromatography is preferable. To perform hydrophobic chromatography, for example, a column packed with a carrier to which phenyl groups are bound (e.g., resin) can be used (e.g., a Phenyl Sepharose column). The composition of the present invention can be produced by performing fractionation, measuring the FADGDH activity and trehalose hydrolase of each fraction by the methods described later, and collecting FADGDH fractions from which a small amount of trehalose hydrolase activity or none of the activity is detected, when performing the various types of chromatography described above.

Examples also include a method using affinity chromatography. For example, when FADGDH is produced using a cell formed by transforming a host with a vector containing a gene that encodes a desired FADGDH, trehalose hydrolase, which has no affinity for nickel columns, can be separated and removed by specifically adsorbing the recombinant FADGDH produced by encoding a histidine tag at the N-terminal or C-terminal portion of the FADGDH gene onto a nickel column, and performing an elution process using a gradient of imidazole concentration. This operation is preferably operated two or more times to achieve a higher removing effect. Alternatively, affinity purification can also be performed using glutathione-S-transferase (GST), maltose-binding protein (MBP), HA, FLAG peptide, or the like as a tag, and trehalose hydrolysis activity is also expected to be eliminated in the same manner.

Of the types of chromatography described above, cation-exchange chromatography is most preferable.

As long as the composition of the present invention has the two attributes described above, other formulations are not particularly limited.

For example, because the composition of the present invention can be applied to a glucose sensor as a glucose-measuring-enzyme preparation, the composition may contain various substances for application to sensors.

The composition of the present invention is also allowed to contain impurities in such an amount as to not pose a problem in glucose measurement (e.g., an enzyme that has no influence on Glucose measurement), as a result of lowering the degree of purification from the standpoint of industrial application or cost-effectiveness.

An example of such substances is a mediator. Examples of mediators include, but are not limited to, quinones, cytochromes, viologens, phenazines, phenoxazines, phenothiazines, ferricyanides, ferredoxins, ferrocenes, and derivatives thereof. More specific examples include benzoquinone/hydroquinone, ferricyane/ferrocyanide (potassium or sodium salts), and ferricinium/ferrocene. Phenazine methosulfate, 1-methoxy-5-methylphenazinium methyl sulfate, 2,6-dichlorophenolindophenol, and the like may also be used. Metal complexes of, for example, osmium, cobalt, and ruthenium can also be used. Biological substances, such as ferredoxins, cytochromes, and thioredoxins, can also be used.

When a compound with a low water solubility as a mediator and an organic solvent for dissolving the compound are used, the stability of the enzyme may be lost, or the enzyme activity may be inactivated. To increase the water solubility, the mediator for use may be modified with a hydrophilic polymer such as polyethylene glycol (PEG). The concentration of the mediator (or its modified product) in a reaction system is preferably about 1 mM to 1 M, more preferably 5 to 500 mM, and still more preferably 10 to 300 mM.

The composition of the present invention may contain any of a variety of buffers for buffering the fluctuations of pH. The buffer is not particularly limited, and may be a substance with a buffering capacity at a pH within the range of preferably pH 5.0 to 9.0. Examples include, but are not limited to, phosphate; various organic acids, such as fumaric acid, maleic acid, glutaric acid, phthalic acid, and citric acid; and Good's buffers, such as MOPS, PIPES, HEPES, MES, and TES.

To enhance the storage stability of FADGDH, the composition of the present invention may suitably contain proteins, such as bovine serum albumin, egg white albumin, and sericin; sugar other than glucose; amino acids; metal salts, such as calcium, magnesium, zinc, and manganese; chelating agents, typically EDTA; and various surfactants, such as TritonX-100, deoxycholic acid, cholic acid, Tween20, Brij35, and Emulgen.

Another embodiment of the present invention is a glucose measurement sensor comprising the composition, or a method for measuring glucose using the composition or the glucose measurement sensor. The principle of glucose measurement using FADGDH, as well as the structure, operating principle, production method, usage, etc., of the glucose measurement sensor have already been established in this technical field. Thus, a person skilled in the art will be able to apply the established findings to the present invention to produce a glucose measurement sensor or to measure glucose using the composition or the glucose measurement sensor, and the embodiments are not particularly limited.

Because of the low content of trehalose degrading enzyme (typically trehalase), trehalose may be added to the glucose measurement sensor of the present invention, for example, for stabilization. Specifically, the sensor of the present invention may contain trehalose. The method for measuring glucose according to the present invention can be performed even when trehalose is present in a sample and/or reagent composition.

The glucose measurement sensor of the present invention may be, for example, a calorimetric sensor or electrochemical sensor. The glucose measurement sensor may also be equipped with an arithmetic unit for calculating a blood glucose concentration based on the signal intensity obtained from a response to glucose and a display for showing the calculated blood glucose concentration. In addition, the glucose measurement sensor may be a sensor onto a reactive layer of which blood or a diluted solution of blood as an analyte is allowed to fall in drops, or the sensor may be equipped with a needle for perforating the skin of a subject to collect blood and/or a flow path for delivering blood; the needle and/or flow path may be attachable. When the sensor has a reactive layer, GDH is preferably contained in the reactive layer. When the sensor is a calorimetric sensor, the sensor may be equipped with a light source lamp and a photometer for measuring the absorbance. When the sensor is an electrochemical sensor, the sensor may contain a working electrode and a counter electrode, or the sensor may be attachable to a chip holding GDH and an electron acceptor on the electrodes. The electrodes for use include carbon electrodes, gold electrodes, silver electrodes, or platinum electrodes, and GDH is immobilized on the electrode(s). The immobilization methods include a method using a crosslinking reagent, a method in which GDH is encapsulated in a polymer matrix, a method in which GDH is coated with a dialysis membrane, and a method using a photocrosslinking polymer, a conductivity polymer, or a redox polymer. GDH may be immobilized together with an electron acceptor within the polymer or immobilized on electrodes by adsorption; alternatively, these immobilizations may be combined. Typically, GDH is immobilized on a carbon electrode using glutaraldehyde and treated with an amine-group-containing reagent to block glutaraldehyde.

When the sensor of the present invention is a colorimetric glucose sensor, a glucose concentration can be measured using the sensor, for example, in the following manner. Specifically, a liquid or solid composition containing at least FADGDH and an electron acceptor is maintained. At this stage, a pH buffer and a coloration reagent are optionally added to the composition. A glucose-containing sample is then added to the composition, and the resultant is subjected to reaction for a predetermined time period. During the reaction, an absorbance that corresponds to the wavelength of maximum absorption of an electron acceptor discolored by reduction or an absorbance that corresponds to the wavelength of maximum absorption of a pigment generated through polymerization by accepting electrons from the electron acceptor is monitored. The glucose concentration of the sample can be calculated from a change in absorbance per a predetermined time when the rate assay is used, or from a change in absorbance to the point at which glucose in the sample has entirely been oxidized when the endpoint method is used, based on a calibration curve prepared beforehand from a glucose solution of standard concentration. As the mediator and coloration reagent usable for this method, 2,6-dichlorophenolindophenol (DCPIP), for example, can be added as an electron acceptor, and glucose can be quantified by monitoring the decrease in absorbance at 600 nm. Also, phenazine methosulfate (PMS) as an electron acceptor and nitrotetrazolium blue (NTB) as a coloration reagent can also be added, and the absorbance at 570 nm is measured to determine the amount of generated diformazan, based on which the glucose concentration can be calculated. Needless to say, the electron acceptor and coloration reagent for use are not limited to these acceptors and reagents. The mediator may be immobilized on electrodes together with the enzyme using a modifier of various functional groups.

When the sensor of the present invention is an electrochemical sensor, a glucose concentration can be measured using the sensor in the following manner. A liquid or solid composition containing FADGDH and an electron acceptor is held on a reactive layer connected to electrodes on the glucose sensor. This composition may further contain a pH buffer, etc. A glucose-containing sample is added to the composition, and the resultant is subjected to reaction, followed by the application of a constant voltage across the electrodes. The current is monitored, and the current accumulated during a predetermined time period from the start of voltage application is summed or the current value after a predetermined time period is passed from the start of voltage application is measured. The glucose concentration of the sample can be calculated from the value on the basis of a calibration curve prepared from a glucose solution of standard concentration.

FADGDH Activity Measurement Method

In this specification, the FADGDH activity is measured in accordance with the following method unless otherwise indicated.

3.0 mL of a reaction solution (34.9 mmol/L of a PIPES-NaOH buffer, 200 mmol/L of D-glucose, 3.24 mmol/L of PMS, 0.10 mmol/L of DCPIP, pH 6.5) is added to a quartz cell, and preheated at 37° C. for 5 minutes. 0.1 mL of a GDH solution is added and mixed, followed by reaction at 37° C. for 5 minutes, during which the absorbance at 600 nm is measured. From the linear section of the change in absorbance, the decrease in absorbance per minute ($\Delta OD_{TEST}$) is calculated. In a blind test, instead of the GDH solution, a buffer solution is added and mixed, and the mixture is incubated at 37° C. for 5 minutes, followed by recording the absorbance at 600 nm in the same manner. From the initial linear section, the decrease in absorbance per minute ($\Delta OD_{BLANK}$) is calculated. These values are applied to the following equation to determine the activity value (U/mL). In this specification, the amount of enzyme that reduces 1 micromole of DCPIP in one minute in the presence of a substrate is defined as 1 U.

$$\text{GDH Activity (U/mL)} = [(\Delta OD_{TEST} - \Delta OD_{BLANK}) \times 3.1 \times \text{Dilution Factor}]/(16.8 \times 1.0 \times 0.1)$$

3.1: The volume of the GDH solution after mixing (mL)
16.8: The millimolar molecular extinction coefficient of DCPIP ($cm^2$/micromole)
1.0: The optical path length (cm)
0.1: The amount of the GDH solution added (mL)

Trehalose Hydrolysis Activity Measurement Method

The trehalose hydrolysis activity defined in the present invention is measured as described below, unless otherwise indicated.

2.9 mL of a reaction solution (84 mmol/L of a sodium citrate buffer, 1 mmol/L of potassium ferricyanide, 10 mM of trehalose, pH 3.5) is added to a quartz cell, and preheated at 37° C. for 5 minutes. 0.1 mL of FADGDH (15000 U/mL) is added thereto and mixed (the final GDH concentration: 500 U/mL), followed by reaction at 37° C. for 5 minutes, during which the absorbance at 405 nm is measured to calculate the decrease in absorbance per minute ($\Delta OD_{TEST}$). In a blind test, instead of the GDH solution, a buffer solution is added and mixed, and the mixture is incubated at 37° C. for 5 minutes, followed by recording the absorbance at 405 nm in the same manner. From the initial linear section, the decrease in absorbance per minute ($\Delta OD_{BLANK}$) is calculated. The value obtained by deducting $\Delta OD_{BLANK}$ from $\Delta OD_{TEST}$ is evaluated as a decrease in absorbance (mABS/min) attributable to oligosaccharide hydrolysis.

Trehalase Content Measurement Method

In this specification, the content of trehalase (%) is calculated by the following equation.

Trehalase Activity/FADGDH Activity×100

In this specification, the trehalase activity is defined as a decrease in absorbance (mABS/min) determined by the "Trehalose Hydrolysis Activity Measurement Method" described above. The FADGDH activity is 500 (U/mL)(the final FADGDH concentration in the activity measurement method described above).

The following describes the present invention as specific Examples, but the present invention is not limited to these Examples.

EXAMPLES

Example 1

Preparing Compositions Containing FADGDH

To evaluate multiple FADGDH-containing compositions as a glucose-measuring-enzyme preparation, compositions containing FADGDH expressed in a variety of hosts were prepared. The prepared compositions were measured for FADGDH activity based on powder weight by the FADGDH activity measurement method described above. Additionally, the FADGDH concentration of each composition was adjusted to measure the oligosaccharide degradation activity as described above. The trehalase activity of each composition was also measured by the method described above, and the content of trehalase was calculated.

Table 1 shows the results.

The host of "FADGDH1" in Table 1 is *Aspergillus oryzae*, and FADGDH1 is derived from *Aspergillus oryzae* (SEQ ID: No. 1). The host of "FADGDH2" in Table 1 is *Aspergillus oryzae*, and FADGDH2 is derived from *Aspergillus terreus* (SEQ ID: No. 2). The host of "FADGDH3" in Table 1 is *Cryptococcus* sp.S-2 (depository number: FERM BP-10961), and FADGDH3 is derived from *Mucor subtilissimus* (SEQ ID: No. 3).

The host of "FADGDH4" in Table 1 is *Cryptococcus* sp.S-2, and FADGDH4 is derived from *Mucor hiemalis* (SEQ ID: No. 4). The host of "FADGDH5" in Table 1 is *Cryptococcus* sp.S-2, and FADGDH5 is derived from *Mucor* RD056860 (SEQ ID: No. 5). "FADGDH6" in Table 1 was obtained by adsorbing "FADGDH5" onto a cation-exchange column (a CM-Sepharose column packed with a carrier to which carboxy methyl groups were bound) and eluting it by chromatography.

TABLE 1

|  | FADGDH Activity (U/mg) | Trehalase Activity (mAbs/min) | Trehalase Content % |
|---|---|---|---|
| FADGDH1 | 628 | N.D. (not detected) | N.D. (not detected) |
| FADGDH2 | 651 | N.D. (not detected) | N.D. (not detected) |
| FADGDH3 | 380 | 9.9 | 1.98 |
| FADGDH4 | 388 | 4 | 0.8 |
| FADGDH5 | 485 | 3.8 | 0.76 |
| FADGDH6 | 520 | N.D. (not detected) | N.D. (not detected) |

As shown in Table 1, the results reveal that oligosaccharide degradation activity was detected in some compositions and not detected in other compositions (there was a difference). The results also reveal that the content of trehalase differs between the compositions. The results further reveal that oligosaccharide degradation activity correlates with the content of trehalase, and that as the content of trehalase increases, the oligosaccharide degradation activity is more likely to increase.

"FADGDH6" in Table 1 was obtained by purifying "FADGDH5" in Table 1 through fractionation by cation-exchange column chromatography (a CM-Sepharose column was used). Purifying FADGDH by a predetermined method could eliminate the oligosaccharide degradation activity and also decrease the content of trehalase.

Example 2

Preparation of Reagent Compositions for Measuring Glucose Using Compositions Containing Different FADGDH and Examination of Blank-Up First, as a reagent for measuring glucose, a solution of the following formulation (pH=7.0) was prepared (control composition).

1 mM of Citric Acid
50 mM of Potassium Ferricyanide
800 U/mL of a Composition Containing FADGDH (the composition shown in Example 1)
1% of Trehalose After this solution was prepared and allowed to stand at 37° C. for 3 hours, a glucose sensor was prepared using this solution. The Glucose sensor was prepared as follows. 5 μL of a 0.5% CMC (carboxymethyl cellulose) solution was dropped onto three electrodes (a working electrode, a counter electrode, and a reference electrode) provided to a disposable chip (DEP-CHIP, BioDevice Technology, Ltd.), and the dropped solution was dried at 50° C. for 10 minutes by heating treatment, followed by further dropping 5 μL of the reagent for measuring glucose prepared by mixing components described above, thereby preparing a sensor chip. This sensor chip was connected to a potentio-galvanostat via a dedicated socket, and 5 μL of physiological saline was added to the composition on the electrodes, followed by the application of voltage at +0.3 V. Then, the current response value was monitored.

Figure 1:
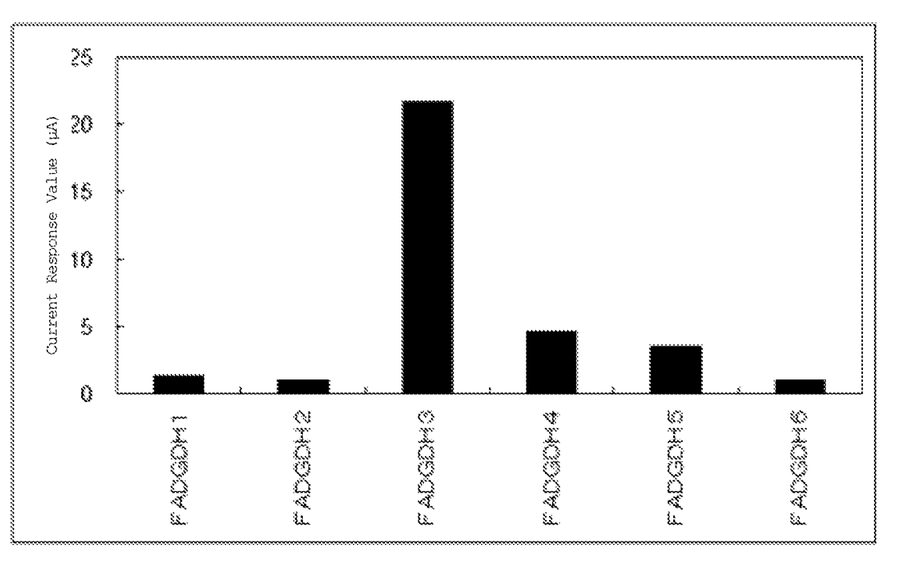
FIG. 1: Preparation of compositions for quantifying glucose using various purified GDHs and examination of blank-up.

Table 2 and FIG. 1 show the results. Table 2 shows measurement results of the current response value along side of the oligosaccharide degradation activity and the content of trehalase of each FADGDH obtained in Example 1.

TABLE 2

|  | Current Response Value (μA) | Trehalase Activity (mAbs/min) | Trehalase Content % |
|---|---|---|---|
| FADGDH1 | 1.2 | N.D. (not detected) | N.D. (not detected) |
| FADGDH2 | 1.0 | N.D. (not detected) | N.D. (not detected) |
| FADGDH3 | 21.6 | 9.9 | 1.98 |
| FADGDH4 | 4.6 | 4 | 0.8 |
| FADGDH5 | 3.5 | 3.8 | 0.76 |
| FADGDH6 | 1.0 | N.D. (not detected) | N.D. (not detected) |

As shown in Table 2 and FIG. 1, the results reveal that the reagent compositions for measuring glucose that exhibit a low oligosaccharide degradation activity or a low content of trehalase can decrease blank-up that appears to be due to hydrolysis of trehalose in the compositions. Specifically, the results reveal that the FADGDH preparation for measuring glucose according to the present invention can decrease the influence of trehalose present in a sensor formulation or in a sample.

INDUSTRIAL APPLICABILITY

The present invention can be provided as a reagent for measuring blood glucose concentrations, a blood glucose sensor, or a kit for quantifying glucose concentrations.

The invention claimed is:

1. A glucose measurement sensor comprising a composition and an electrode,
wherein the composition comprises flavin adenine dinucleotide-dependent glucose dehydrogenase, a mediator, and trehalose, and does not comprise cytochromes,
wherein the flavin adenine dinucleotide-dependent glucose dehydrogenase is derived from a microorganism belonging to genus *Aspergillus* and is obtained by recombinant expression using *Aspergillus oryzae* as a host, and
wherein the flavin adenine dinucleotide-dependent glucose dehydrogenase is immobilized on the electrode.

2. A method for measuring glucose comprising contacting a sample with a glucose measurement sensor comprising
(i) a composition comprising flavin adenine dinucleotide-dependent glucose dehydrogenase, a mediator, and trehalose and
(ii) an electrode,
wherein the flavin adenine dinucleotide-dependent glucose dehydrogenase is derived from a microorganism belonging to genus *Aspergillus* and is obtained by recombinant expression using *Aspergillus oryzae* as a host.

3. A method for measuring glucose comprising contacting a sample with the glucose measurement sensor according to claim 1.

4. The glucose measurement sensor of claim 1, wherein the composition has a trehalase content of 2.0% or less.

5. The glucose measurement sensor of claim 1, wherein the mediator is selected from the group consisting of benzoquinone, hydroquinone, ferricyane potassium, ferrocyanide potassium, ferricyane sodium, ferrocyanide sodium, ferricinium, ferrocene, phenazine methosulfate, 1-methoxy-5-methylphenazinium methyl sulfate, 2,6-dichlorophenolindophenol, osmium complex, cobalt complex, ruthenium complex, ferredoxins, and thioredoxins.

6. The method of claim 2, wherein the composition has a trehalase content of 2.0% or less.

7. The method of claim 2, wherein the composition does not comprise cytochromes.

8. The method of claim 2, wherein the mediator is selected from the group consisting of benzoquinone, hydroquinone, ferricyane potassium, ferrocyanide potassium, ferricyane sodium, ferrocyanide sodium, ferricinium, ferrocene, phenazine methosulfate, 1-methoxy-5-methylphenazinium methyl sulfate, 2,6-dichlorophenolindophenol, osmium complex, cobalt complex, ruthenium complex, ferredoxins, and thioredoxins.

9. The method of claim 3, wherein the composition has a trehalase content of 2.0% or less.

10. The method of claim 3, wherein the mediator is selected from the group consisting of benzoquinone, hydroquinone, ferricyane potassium, ferrocyanide potassium, ferricyane sodium, ferrocyanide sodium, ferricinium, ferrocene, phenazine methosulfate, 1-methoxy-5-methylphenazinium methyl sulfate, 2,6-dichlorophenolindophenol, osmium complex, cobalt complex, ruthenium complex, ferredoxins, and thioredoxins.

11. The glucose measurement sensor of claim 1, wherein the composition has a trehalase content of 1.0% or less.

12. The glucose measurement sensor of claim 1, wherein the composition has a trehalase content of 0.8% or less.

13. The glucose measurement sensor of claim 1, wherein the composition has a trehalase content of 0.76% or less.

14. The method of claim 2, wherein the composition has a trehalase content of 1.0% or less.

15. The method of claim 2, wherein the composition has a trehalase content of 0.8% or less.

16. The method of claim 2, wherein the composition has a trehalase content of 0.76% or less.

17. The method of claim 3, wherein the composition has a trehalase content of 1.0% or less.

18. The method of claim 3, wherein the composition has a trehalase content of 0.8% or less.

19. The method of claim 3, wherein the composition has a trehalase content of 0.76% or less.

20. The glucose measurement sensor of claim 1, wherein the microorganism belonging to genus *Aspergillus* is *Aspergillus oryzae* or *Aspergillus terreus*.

21. The glucose measurement sensor of claim 1, wherein the microorganism belonging to genus *Aspergillus* is *Aspergillus terreus*.

* * * * *

SEQUENCE LISTING

<160> NUMBER OF SEQ ID NOS: 5

<210> SEQ ID NO 1
<211> LENGTH: 593
<212> TYPE: PRT
<213> ORGANISM: Aspergillus oryzae

<400> SEQUENCE: 1

```
Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
    290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Gly Tyr Gly Val Leu Ala
            340                 345                 350

Gly Ala Ser Thr Val Thr Tyr Pro Ser Ile Ser Asp Val Phe Gly Asn
        355                 360                 365
```

```
Glu Thr Asp Ser Ile Val Ala Ser Leu Arg Ser Gln Leu Ser Asp Tyr
    370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Asn Ala Val
            420                 425                 430

Ser Ser Glu Phe Trp Gly Leu Pro Phe Ala Arg Gly Asn Ile His
        435                 440                 445

Ile Ser Ser Asn Asp Pro Thr Ala Pro Ala Ile Asn Pro Asn Tyr
    450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
                500                 505                 510

Lys Trp Val Glu Trp Leu Lys Ala Asn Tyr Arg Ser Asn Phe His Pro
            515                 520                 525

Val Gly Thr Ala Ala Met Met Pro Arg Ser Ile Gly Gly Val Val Asp
        530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 2
<211> LENGTH: 568
<212> TYPE: PRT
<213> ORGANISM: Aspergillus terreus

<400> SEQUENCE: 2

Met Lys Tyr Asp Tyr Ile Val Ile Gly Gly Gly Thr Ser Gly Leu Ala
1               5                   10                  15

Val Ala Asn Arg Leu Ser Glu Asp Pro Ser Val Asn Val Leu Ile Leu
            20                  25                  30

Glu Ala Gly Gly Ser Val Trp Asn Asn Pro Asn Val Thr Asn Val Asn
        35                  40                  45

Gly Tyr Gly Leu Ala Phe Gly Ser Asp Ile Asp Trp Gln Tyr Gln Ser
    50                  55                  60

Val Asn Gln Pro Tyr Gly Gly Asn Val Ser Gln Val Leu Arg Ala Gly
65                  70                  75                  80

Lys Ala Leu Gly Gly Thr Ser Thr Ile Asn Gly Met Ala Tyr Thr Arg
                85                  90                  95

Ala Glu Asp Val Gln Ile Asp Ala Trp Glu Thr Ile Gly Asn Thr Gly
            100                 105                 110

Trp Thr Trp Lys Asn Leu Phe Pro Tyr Tyr Arg Lys Ser Glu Asn Phe
        115                 120                 125

Thr Val Pro Thr Lys Ser Gln Thr Ser Leu Gly Ala Ser Tyr Glu Ala
    130                 135                 140
```

```
Gly Ala His Gly His Glu Gly Pro Leu Asp Val Ala Phe Thr Gln Ile
145                 150                 155                 160

Glu Ser Asn Asn Leu Thr Thr Tyr Leu Asn Arg Thr Phe Gln Gly Met
            165                 170                 175

Gly Leu Pro Trp Thr Glu Asp Val Asn Gly Gly Lys Met Arg Gly Phe
            180                 185                 190

Asn Leu Tyr Pro Ser Thr Val Asn Leu Glu Glu Tyr Val Arg Glu Asp
            195                 200                 205

Ala Ala Arg Ala Tyr Tyr Trp Pro Tyr Lys Ser Arg Pro Asn Leu His
210                 215                 220

Val Leu Leu Asn Thr Phe Ala Asn Arg Ile Val Trp Asp Gly Glu Ala
225                 230                 235                 240

Arg Asp Gly Asp Ile Thr Ala Ser Gly Val Glu Ile Thr Ser Arg Asn
                245                 250                 255

Gly Thr Val Arg Val Ile Asn Ala Glu Lys Glu Val Ile Val Ser Ala
                260                 265                 270

Gly Ala Leu Lys Ser Pro Ala Ile Leu Glu Leu Ser Gly Ile Gly Asn
                275                 280                 285

Pro Ser Val Leu Asp Lys Tyr Asn Ile Pro Val Lys Val Asn Leu Pro
290                 295                 300

Thr Val Gly Glu Asn Leu Gln Asp Gln Val Asn Ser His Met Asp Ala
305                 310                 315                 320

Ser Gly Asn Thr Ser Ile Ser Gly Thr Lys Ala Val Ser Tyr Pro Asp
                325                 330                 335

Val Tyr Asp Val Phe Gly Asp Glu Ala Glu Ser Val Ala Lys Gln Ile
                340                 345                 350

Arg Ala Ser Leu Lys Gln Tyr Ala Ala Asp Thr Ala Gln Ala Asn Gly
                355                 360                 365

Asn Ile Met Lys Ala Ala Asp Leu Glu Arg Leu Phe Glu Val Gln Tyr
                370                 375                 380

Asp Leu Ile Phe Lys Gly Arg Val Pro Ile Ala Glu Val Leu Asn Tyr
385                 390                 395                 400

Pro Gly Ser Ala Thr Ser Val Phe Ala Glu Phe Trp Ala Leu Leu Pro
                405                 410                 415

Phe Ala Arg Gly Ser Val His Ile Gly Ser Ser Asn Pro Val Glu Phe
                420                 425                 430

Pro Val Ile Asn Pro Asn Tyr Phe Met Leu Asp Trp Asp Ala Lys Ser
                435                 440                 445

Tyr Val Ala Val Ala Lys Tyr Ile Arg Arg Ser Phe Glu Ser Tyr Pro
                450                 455                 460

Leu Ser Ser Ile Val Lys Glu Ser Thr Pro Gly Tyr Asp Val Ile Pro
465                 470                 475                 480

Arg Asn Ala Ser Glu Gln Ser Trp Lys Glu Trp Val Phe Asp Lys Asn
                485                 490                 495

Tyr Arg Ser Asn Phe His Pro Val Gly Thr Ala Ala Met Met Pro Arg
                500                 505                 510

Glu Ile Gly Gly Val Val Asp Glu Arg Leu Asn Val Tyr Gly Thr Thr
                515                 520                 525

Asn Val Arg Val Val Asp Ala Ser Val Leu Pro Phe Gln Val Cys Gly
                530                 535                 540

His Leu Val Ser Thr Leu Tyr Ala Val Ala Glu Arg Ala Ala Asp Leu
545                 550                 555                 560

Ile Lys Ala Asp Ala Gly Arg Arg
```

565

<210> SEQ ID NO 3
<211> LENGTH: 633
<212> TYPE: PRT
<213> ORGANISM: Mucor subtilissimus

<400> SEQUENCE: 3

```
Met Arg Leu Ser Leu Ala Ile Leu Ser Leu Thr Ser Ala Leu Val Thr
1               5                   10                  15

Val Thr Ser Ala Gln Gln Asn Gly Thr Ser Asn Asp Thr Tyr Asp Tyr
            20                  25                  30

Val Ile Val Gly Gly Gly Val Gly Gly Leu Ser Leu Ala Ser Arg Leu
        35                  40                  45

Ser Glu Asp Lys Gly Val Thr Val Ala Val Leu Glu Ser Gly Pro Tyr
    50                  55                  60

Ala Asp Asp Arg Phe Val Val Tyr Ala Pro Gly Met Tyr Gly Gln Ala
65                  70                  75                  80

Val Gly Thr Glu Leu Cys Pro Leu Leu Pro Thr Val Pro Gln Val Gly
                85                  90                  95

Met Asn Asn Arg Thr Ile Thr Ile Ala Thr Gly Arg Leu Leu Gly Gly
            100                 105                 110

Gly Ser Ala Val Asn Gly Leu Val Trp Thr Arg Gly Ala Met Lys Asp
        115                 120                 125

Phe Asp Ala Trp Glu Glu Leu Gly Asn Pro Gly Trp Asn Gly Lys Thr
    130                 135                 140

Met Phe Lys Tyr Phe Lys Lys Ile Glu Asn Phe His Pro Pro Thr Glu
145                 150                 155                 160

Glu Gln Val Gln Tyr Gly Ala Thr Tyr Gln Lys Asn Val His Gly Ser
                165                 170                 175

Gly Gly Pro Ile Asp Ile Ser Phe Pro Val Phe Glu Phe Pro Gln Ser
            180                 185                 190

Ala Asn Trp Asn Ala Ser Leu Ala Tyr Leu Asn Phe Thr His Gln Gln
        195                 200                 205

Asp Leu Leu Asn Gly Ser Leu His Gly Tyr Ser Thr Thr Pro Asn Thr
    210                 215                 220

Leu Asn Pro Glu Thr Ala Arg Arg Ala Asp Ala Tyr Ala Gly Tyr Ile
225                 230                 235                 240

Gln Pro Asn Val Asn Arg Thr Asn Leu Ala Val Leu Ala Asn His Thr
                245                 250                 255

Val Ser Arg Ile Gln Phe Glu Lys Ser Asn Gly Ser Gln Pro Leu Lys
            260                 265                 270

Ala Ile Gly Val Glu Trp Tyr Thr Thr Gly Gly Asp Lys Ser Thr Lys
        275                 280                 285

Gln Thr Ile Lys Ala Arg Arg Glu Val Ile Ile Ser Ser Gly Ala Ile
    290                 295                 300

Gly Ser Pro Lys Leu Leu Glu Val Ser Gly Ile Gly Asn Lys Gln Ile
305                 310                 315                 320

Val Thr Ala Ala Gly Val Glu Ser Leu Ile Asp Leu Pro Gly Val Gly
                325                 330                 335

Ser Asn Met Gln Asp His Val His Ala Val Thr Val Ser Thr Thr Asn
            340                 345                 350

Ile Glu Gly Tyr Thr Thr Asn Ser Val Phe Thr Asn Glu Thr Leu Ala
        355                 360                 365
```

```
Gln Glu Gln Lys Asp Leu Tyr Tyr Asn Asn Lys Thr Gly Ile Trp Thr
    370                 375                 380
Thr Thr Pro Asn Asn Leu Gly Tyr Pro Ser Pro Ser Gln Leu Phe Thr
385                 390                 395                 400
Asn Thr Thr Phe Arg Ser Gly Lys Gln Phe Ala Ala Met Ile Arg Asn
                405                 410                 415
Ser Thr Asp Lys Tyr Ala Gln Tyr Tyr Ala Ser Thr Lys Asn Ala Thr
            420                 425                 430
Asn Ile Gln Leu Leu Lys Lys Gln Tyr Ala Ile Val Ala Arg Arg Tyr
        435                 440                 445
Glu Glu Asp Tyr Ile Ser Pro Ile Glu Ile Asn Phe Thr Pro Gly Tyr
    450                 455                 460
Gly Gly Thr Gly Glu Val Asp Leu Gln Asn Asn Lys Tyr Gln Thr Val
465                 470                 475                 480
Asn His Val Leu Val Ala Pro Leu Ser Arg Gly Tyr Thr His Ile Asn
                485                 490                 495
Ser Ser Asp Ile Glu Asp Pro Val Val Ile Asp Pro Gln Tyr Tyr Ser
            500                 505                 510
His Pro Leu Asp Val Asp Val His Val Ala Ser Thr Gln Leu Ala Arg
        515                 520                 525
Ser Ile Leu Asn Ala Pro Ala Leu Ala Ala Ile Asn Ser Gly Glu Val
    530                 535                 540
Glu Pro Gly Glu Lys Ile Gln Thr Asp Gln Asp Val Arg Lys Trp Leu
545                 550                 555                 560
Ser Asp Asn Val Arg Ser Asp Trp His Pro Val Gly Thr Cys Ala Met
                565                 570                 575
Leu Pro Lys Gly Leu Gly Gly Val Val Asp Ser Asn Leu Lys Val Tyr
            580                 585                 590
Gly Thr Ala Asn Leu Arg Val Val Asp Ala Ser Ile Ile Pro Leu Glu
        595                 600                 605
Ile Ser Ser His Leu Met Gln Pro Val Tyr Ala Val Ser Glu Arg Ala
    610                 615                 620
Ala Asp Ile Ile Lys Gly Ser Arg Asn
625                 630

<210> SEQ ID NO 4
<211> LENGTH: 635
<212> TYPE: PRT
<213> ORGANISM: Mucor hiemalis

<400> SEQUENCE: 4

Met Lys Ile Ser Val Ala Ile Val Thr Ile Ala Ala Ala Phe Ala Ser
1               5                   10                  15
Phe Ala Asn Ala Gln Lys Thr Ala Thr Ser Asn Thr Tyr Asp Tyr Val
                20                  25                  30
Ile Val Gly Gly Gly Val Gly Gly Leu Ala Leu Ala Ser Arg Leu Ser
            35                  40                  45
Glu Asp Lys Ser Val Thr Val Ala Val Leu Glu Ala Gly Pro Asn Ala
        50                  55                  60
Asp Glu Gln Phe Val Val Tyr Ala Pro Gly Met Tyr Gly Gln Ala Val
65                  70                  75                  80
Gly Thr Asp Leu Cys Pro Leu Arg Pro Thr Val Pro Gln Glu Ala Met
                85                  90                  95
Asn Asn Arg Thr Leu Thr Ile Ala Thr Gly Lys Leu Leu Gly Gly Gly
            100                 105                 110
```

```
Ser Ala Ile Asn Gly Leu Val Trp Thr Arg Gly Ala Leu Lys Asp Phe
            115                 120                 125
Asp Ala Trp Glu Glu Leu Gly Asn Pro Gly Trp Asn Gly Arg Thr Met
        130                 135                 140
Phe Lys Tyr Phe Lys Lys Val Glu Arg Phe His Pro Thr Lys Ala
145                 150                 155                 160
Gln Val Gln Tyr Gly Ala Thr Tyr Gln Lys Gly Val His Gly Lys Asn
                165                 170                 175
Gly Arg Ile Asp Ile Ser Phe Pro Glu Phe Gln Phe Pro Gln Ser Ala
                180                 185                 190
Asn Trp Asn Ala Ser Leu Ala Thr Leu Asp Phe Thr His Gln Gln Asp
            195                 200                 205
Leu Leu Asn Gly Ser Leu His Gly Tyr Ser Thr Thr Pro Asn Thr Leu
        210                 215                 220
Asp Pro Lys Thr Ala Arg Arg Val Asp Ser Tyr Thr Gly Tyr Ile Ala
225                 230                 235                 240
Pro Phe Val Ser Arg Lys Asn Leu Phe Val Leu Ala Asn His Thr Val
                245                 250                 255
Ser Arg Ile Gln Phe Lys Pro Lys Asn Gly Thr Glu Leu Leu Lys Ala
            260                 265                 270
Val Gly Val Glu Trp Tyr Thr Thr Gly Asp Asn Ser Asn Lys Gln Thr
        275                 280                 285
Ile Lys Ala Arg Arg Glu Val Ile Val Ser Ser Gly Ser Ile Gly Ser
                290                 295                 300
Pro Lys Leu Leu Glu Ile Ser Gly Ile Gly Asn Lys Asp Ile Val Thr
305                 310                 315                 320
Ala Ala Gly Val Gln Ser Leu Ile Asp Leu Pro Gly Val Gly Ser Asn
                325                 330                 335
Met Gln Asp His Val His Ala Val Thr Val Ser Thr Thr Asn Ile Thr
            340                 345                 350
Gly Phe Thr Thr Asp Ser Val Phe Gln Asn Glu Thr Leu Ala Glu Glu
        355                 360                 365
Gln Arg Gln Gln Tyr Tyr Asn Asn Lys Thr Gly Ile Trp Thr Thr Thr
        370                 375                 380
Pro Asn Asn Leu Gly Tyr Pro Ser Pro Ser Gln Leu Phe Asp Gly Thr
385                 390                 395                 400
Ser Phe Glu Ser Gly Gln Ala Phe Ala Asn Arg Ile Arg Asn Ser Thr
                405                 410                 415
Asp Gln Trp Ala Glu Tyr Tyr Ala Ser Thr Asn Ala Thr Asn Ile Glu
            420                 425                 430
Leu Leu Lys Lys Gln Tyr Ala Ile Val Ala Ser Arg Tyr Glu Glu Asn
        435                 440                 445
Tyr Leu Ser Pro Ile Glu Ile Asn Phe Thr Pro Gly Tyr Gly Gly Thr
    450                 455                 460
Thr Asp Val Asp Leu Lys Asn Asn Lys Tyr Gln Thr Val Asn His Val
465                 470                 475                 480
Leu Ile Ala Pro Leu Ser Arg Gly Tyr Thr His Ile Asn Ser Ser Asn
                485                 490                 495
Ile Glu Asp Pro Val Val Ile Asn Pro Gln Tyr Tyr Thr His Pro Met
            500                 505                 510
Asp Val Asp Val His Ile Ala Ser Thr Lys Leu Ala Arg Arg Ile Leu
        515                 520                 525
```

```
Gly Ala Glu Pro Gly Leu Ala Ser Ile Asn Ser Gly Glu Ile Gln Pro
            530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
            580                 585                 590

Ala Asn Leu Arg Val Val Asp Ala Ser Ile Met Pro Leu Glu Ile Ser
                595                 600                 605

Ser His Leu Met Gln Pro Thr Tyr Gly Val Ala Glu Lys Ala Ala Asp
610                 615                 620

Ile Ile Lys Met Ser Arg Lys Asn Asn Asn
625                 630                 635

<210> SEQ ID NO 5
<211> LENGTH: 631
<212> TYPE: PRT
<213> ORGANISM: Mucor RD056860

<400> SEQUENCE: 5

Met Arg Leu Ser Val Ala Ile Leu Thr Leu Thr Ser Ala Leu Ala Ser
1               5                   10                  15

Val Thr Ser Ala Gln Gln Asn Asn Thr Asp Thr Tyr Asp Tyr Val Ile
            20                  25                  30

Val Gly Gly Gly Val Gly Gly Leu Ala Leu Ala Ser Arg Leu Ser Glu
        35                  40                  45

Asp Lys Asn Val Thr Val Ala Val Leu Glu Ser Gly Pro Tyr Ala Asp
    50                  55                  60

Asp Lys Phe Val Val Tyr Ala Pro Gly Met Tyr Gly Gln Ala Val Gly
65                  70                  75                  80

Thr Asp Leu Cys Pro Leu Leu Pro Thr Val Pro Gln Pro Ser Met Asn
                85                  90                  95

Asn Arg Thr Ile Thr Ile Ala Thr Gly Arg Leu Leu Gly Gly Gly Ser
            100                 105                 110

Ala Val Asn Gly Leu Val Trp Thr Arg Gly Ala Met Lys Asp Phe Asp
        115                 120                 125

Ala Trp Gln Glu Leu Gly Asn Pro Gly Trp Asn Gly Thr Thr Met Phe
    130                 135                 140

Lys Tyr Phe Lys Lys Ile Glu Asn Phe His Pro Pro Thr Glu Glu Gln
145                 150                 155                 160

Ile Gln Tyr Gly Ala Thr Tyr Asn Lys Ser Val His Gly Phe Asn Gly
                165                 170                 175

Pro Ile Asp Ile Ala Phe Pro Val Phe Glu Phe Pro Gln Ser Ala Asn
            180                 185                 190

Trp Asn Ala Ser Leu Ala His Leu Asn Phe Thr Arg Arg Gln Asp Leu
        195                 200                 205

Leu Asp Gly Ser Leu His Gly Tyr Ser Thr Thr Pro Asn Thr Leu Asn
    210                 215                 220

Pro Gln Thr Ala Arg Arg Ala Asp Ala Tyr Ala Gly Tyr Ile Gln Pro
225                 230                 235                 240

Asn Val Asn Arg Thr Asn Leu Ala Val Leu Ala Asn His Thr Val Ser
                245                 250                 255

Arg Ile Gln Phe Glu Ala Arg Asn Gly Ser Gln Pro Leu Lys Ala Ile
            260                 265                 270
```

-continued

```
Gly Val Glu Trp Tyr Thr Thr Gly Gly Asp Lys Thr Ser Lys Gln Thr
        275                 280                 285
Ile Lys Ala Arg Arg Glu Ile Ile Leu Ser Ser Gly Ala Ile Gly Ser
290                 295                 300
Pro Lys Leu Leu Glu Val Ser Gly Ile Gly Asn Lys Ala Ile Val Thr
305                 310                 315                 320
Ala Ala Gly Val Gln Ser Leu Ile Asp Leu Pro Gly Val Gly Ser Asn
                325                 330                 335
Met Gln Asp His Val His Ala Val Thr Val Ser Thr Thr Asn Ile Asp
            340                 345                 350
Gly Tyr Thr Thr Asn Ser Val Phe Thr Asn Glu Thr Leu Ala Gln Glu
        355                 360                 365
Gln Lys Asp Leu Tyr Tyr Asn Asn Lys Thr Gly Ile Trp Thr Thr Thr
370                 375                 380
Pro Asn Asn Leu Gly Tyr Pro Ser Pro Ser Gln Leu Phe Thr Asn Thr
385                 390                 395                 400
Thr Phe Lys Ser Gly Lys Glu Phe Ala Ala Met Ile Arg Asn Ser Thr
                405                 410                 415
Asp Lys Tyr Ala Gln Tyr Ala Ala Asn Asn Ala Thr Asn Val Glu
            420                 425                 430
Leu Leu Lys Lys Gln Tyr Ser Ile Val Ala Arg Arg Tyr Glu Glu Asn
        435                 440                 445
Tyr Ile Ser Pro Ile Glu Ile Asn Phe Thr Pro Gly Tyr Gly Gly Thr
        450                 455                 460
Gly Met Ala Asp Leu Gln Asn Lys Lys Tyr Gln Thr Val Asn His Val
465                 470                 475                 480
Leu Val Ala Pro Leu Ser Arg Gly Tyr Thr His Ile Asn Ser Ser Asp
                485                 490                 495
Ile Glu Asp Pro Val Val Ile Asp Pro Gln Tyr Tyr Ser His Pro Leu
            500                 505                 510
Asp Val Asp Val His Val Ala Ser Thr Gln Leu Ala Arg Ser Ile Leu
        515                 520                 525
Asn Ala Pro Gly Leu Ala Ser Ile Asn Ser Gly Glu Val Glu Pro Gly
530                 535                 540
Glu Lys Val Gln Ser Asp Glu Asp Val Arg Lys Trp Leu Ser Asp Asn
545                 550                 555                 560
Val Arg Ser Asp Trp His Pro Val Gly Thr Cys Ala Met Leu Pro Arg
                565                 570                 575
Lys Leu Gly Gly Val Val Asp Ser Lys Leu Lys Val Tyr Gly Thr Ala
            580                 585                 590
Asn Leu Arg Ile Val Asp Ala Ser Ile Ile Pro Leu Glu Ile Ser Ser
        595                 600                 605
His Leu Met Gln Pro Val Tyr Ala Val Ser Glu Arg Ala Ala Asp Ile
    610                 615                 620
Ile Lys Ser Ser Ser Lys Lys
625                 630
```